United States Patent
Fujieda

[11] Patent Number: 5,861,937
[45] Date of Patent: Jan. 19, 1999

[54] OPHTHALMIC APPARATUS

[75] Inventor: Masanao Fujieda, Gamagori, Japan

[73] Assignee: Nidek Co., Ltd., Gamagori, Japan

[21] Appl. No.: 84,093

[22] Filed: May 26, 1998

[30] Foreign Application Priority Data

May 30, 1997 [JP] Japan .................................... 9-157695
Mar. 31, 1998 [JP] Japan .................................. 10-223533

[51] Int. Cl.⁶ ...................................................... A61B 3/00
[52] U.S. Cl. ........................................................... 351/204
[58] Field of Search ..................................... 351/200, 204, 351/205, 211, 212, 246

[56] References Cited

U.S. PATENT DOCUMENTS

| | | |
|---|---|---|
| 5,463,430 | 10/1995 | Isogai et al. . |
| 5,757,460 | 5/1998 | Cockley .................................. 351/205 |
| 5,784,145 | 7/1998 | Ghodse et al. .......................... 351/205 |

FOREIGN PATENT DOCUMENTS

| | | |
|---|---|---|
| 0 836 830 A1 | 4/1998 | European Pat. Off. . |
| A-61-255634 | 11/1986 | Japan . |
| A-2-265525 | 10/1990 | Japan . |
| A-10-108836 | 4/1998 | Japan . |
| A-10-108837 | 4/1998 | Japan . |

*Primary Examiner*—George Manuel
*Attorney, Agent, or Firm*—Oliff & Berridge, PLC

[57] ABSTRACT

An ophthalmic apparatus having an examining unit which examines an eye to be examined, the apparatus comprising an alignment device for aligning the examining unit with each of a right eye and a left eye, including a target optical system which forms an alignment target on one eye, a corneal reflex forming device including an emitting optical system by which a corneal reflex is formed on the other eye, in which the emitting optical system emitting a luminous flux on relatively wide area where is defined based on dispersion of an interpupillary distance of an examinee, and an optical axis of the emitting optical system and an optical axis of the examining unit being spaced at a predetermined distance, a detecting optical system for detecting a corneal reflection being in a direction intersecting with the optical axis of the emitting optical system, including a limiting device which limits incidence of the corneal reflection and a positional detecting device which detects a position of the limited corneal reflection, and a calculating device for judging whether the aligned eye is a right eye or a left eye and/or calculating an interpupillary distance thereof, based on results detected by the detecting optical system.

20 Claims, 9 Drawing Sheets

A ROTATING DIRECTION

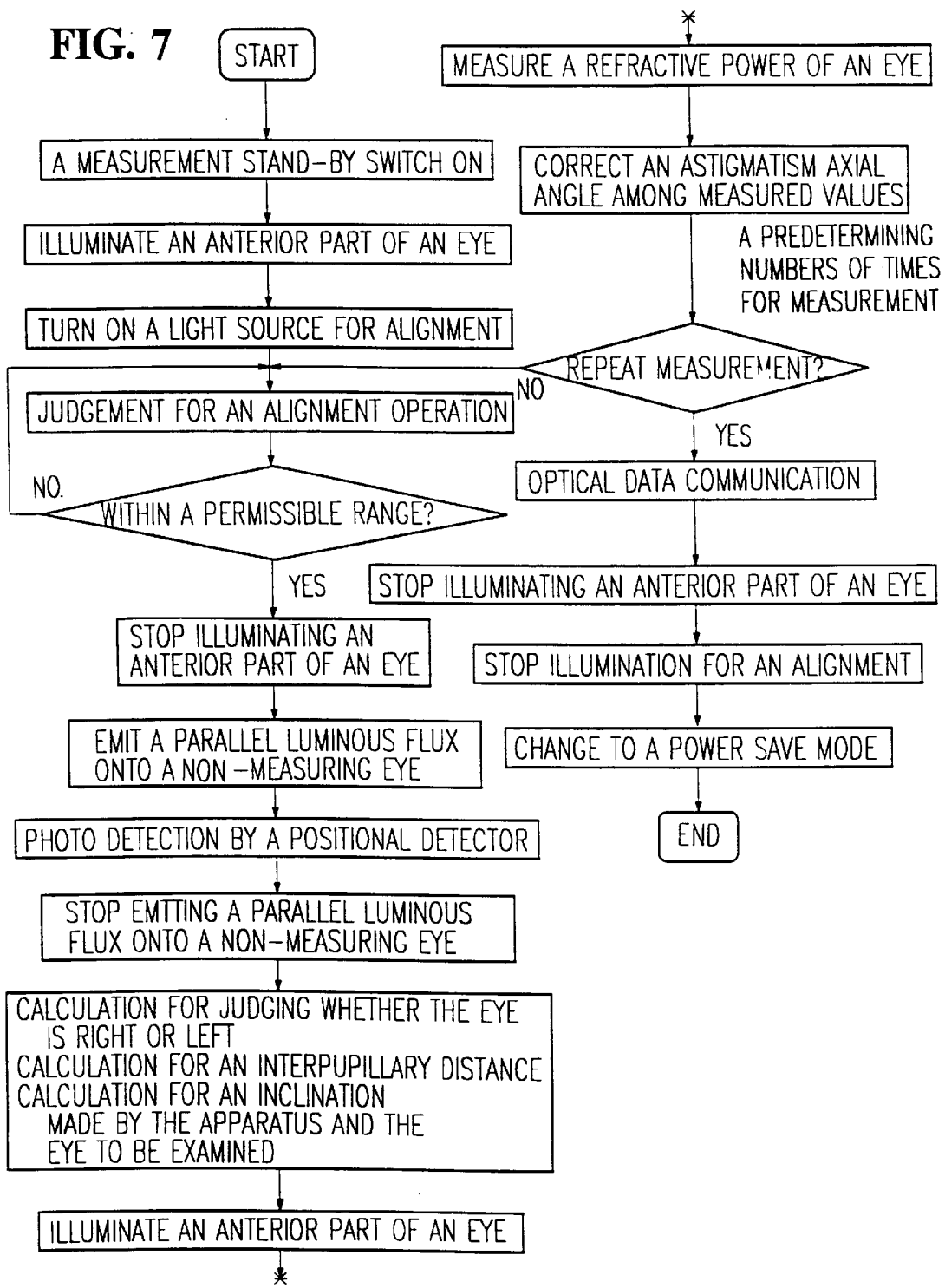

A HORIZONTAL REFERENCE LINE

A HORIZONTAL REFERENCE LINE

OPHTHALMIC APPARATUS

BACKGROUND OF THE INVENTION

1. Field of the Invention

The present invention relates to an ophthalmic apparatus, and more particularly to an ophthalmic apparatus which examines and measures an eye to be examined, such as an apparatus for measuring an objective refractive power, an apparatus for measuring a corneal shape, and the like.

2. Description of Related Art

In conventional art, a setting-type apparatus is widely known as an ophthalmic apparatus such as an apparatus for measuring an objective refractive power, and the like. The setting-type apparatus is configured so that an examining-measuring part can be moved relatively to a fixation base. In generally, the setting-type apparatus is used by an examiner as following, firstly, the examiner makes the examining-measuring part move relative to an eye to be examined by operating a joystick or the like, then, makes the examining-measuring part be aligned with the eye, after that the examiner examines and/or measures the eye one by one. Therefore, referring to such ophthalmic apparatus, an interpupillary distance can be known by obtaining an amount of a lateral movement of the examining-measuring part at the time when condition is changed from which one eye is aligned to which the other eye is aligned. Further, whether the eye is a right eye or a left eye can be also known by detecting whether the examining-measuring part has moved to a right direction or a left direction relative to the center of the fixation base.

On the other hand, in case of using above mentioned setting-type ophthalmic apparatus, it is difficult to examine each eye of an infancy, that of a lying patient, that of an animal and the like, and it is inconvenient to bring it to another place, therefore, a handheld-type ophthalmic apparatus has been proposed recently. The handheld-type ophthalmic apparatus does not has a function to judge whether an eye is a right eye or a left eye based on a movement of an examining-measuring part though above mentioned setting-type apparatus has such function, therefore, whether the examiner examines and/or measures a right eye or a left eye is recognized by inputting a data indicating a right eye or a left eye with using a switch or the like.

However, an operation for inputting a data with using a switch in order to judge whether an eye is a right eye or a left eye is complicated, and the examiner sometimes forgets inputting a data, thereby resulting in a measurement error. In addition, in case of using a handheld-type apparatus, since an amount of a lateral movement while aligning can not be obtained, therefore, an interpupillary distance of the examinee could not be measured.

SUMMARY OF THE INVENTION

The present invention has been made in view of the above circumstances and has an object to overcome the above problems and to provide an ophthalmic apparatus for which an operation for inputting a data is not necessary in order to judge whether an eye is a right eye or a left eye, further, to provide an ophthalmic apparatus which can measure an interpupillary distance of the examinee without using an amount of a lateral movement obtained by aligning the eye one by one.

Also, another object of the present invention is to provide a handheld-type ophthalmic apparatus by which an examiner can operate easily.

Additional objects and advantages of the invention will be set forth in part in the description which follows and in part will be obvious from the description, or may be learned by practice of the invention. The objects and advantages of the invention may be realized and attained by means of the instrumentalities and combinations particularly pointed out in the appended claims.

To achieve the objects and in accordance with the purpose of the present invention, as embodied and broadly described herein, an ophthalmic apparatus having an examining unit which examines an eye to be examined, the apparatus comprises alignment means for aligning the examining unit with each of a right eye and a left eye, including a target optical system which forms an alignment target on one eye, corneal reflex forming means including an emitting optical system by which a corneal reflex is formed on the other eye, in which the emitting optical system emitting a luminous flux on relatively wide area where is defined based on dispersion of an interpupillary distance of an examinee, and an optical axis of the emitting optical system and an optical axis of the examining unit being spaced at a predetermined distance, a detecting optical system for detecting a corneal reflection being in a direction intersecting with the optical axis of the emitting optical system, including limiting means which limits incidence of the corneal reflection and positional detecting means which detects a position of the limited corneal reflection, and calculating means for judging whether the aligned eye is a right eye or a left eye and/or calculating an interpupillary distance thereof, based on results detected by the detecting optical system.

Another aspect of the ophthalmic apparatus of the present invention comprising an alignment target projecting optical system for projecting an alignment target onto a measuring eye in order to align a measuring optical system with the measuring eye, a distance-target projecting optical system for projecting a distance target onto the measuring eye in order to detect a working distance relative to the measuring eye, and a target detecting optical system for detecting respective corneal reflex formed by the both projecting optical systems, the apparatus comprises a front target-detecting optical system for a measuring eye for detecting a part of a luminous flux reflected by the cornea from the measuring eye, which is caused by the alignment target projecting optical system, an emitting optical system for a non-measuring eye for emitting a luminous flux on a non-measuring eye, a front target-detecting optical system for a non-measuring eye for detecting a luminous flux reflected by the cornea from the non-measuring eye, which is caused by the emitting optical system for a non-measuring eye, judging means for judging whether the measuring eye is a right eye or a left eye, based on a detected signal from the front target-detecting optical system for a non-measuring eye, and calculating means for calculating an interpupillary distance between the measuring eye and the non-measuring eye, based on detected signals from the both front target-detecting optical systems and the detected working distance.

According to the present invention, an operation for inputting data is not necessary in order to judge whether the eye to be examined is a right eye or a left eye, further, it is capable of measuring an interpupillary distance of the examinee only based on an alignment of only one eye. Such ophthalmic apparatus is particularly suitable for a handheld-type.

BRIEF DESCRIPTION OF THE DRAWINGS

The accompanying drawings, which are incorporated in and constitute a part of this specification, illustrate embodiments of the present invention and, together with the description, serve to explain the objects, advantages and principles of the invention. In the drawings.

FIG. 7 is a flowchart for illustrating an operation of an apparatus according to the preferred embodiment of the present invention;

DETAILED DESCRIPTION OF THE PREFERRED EMBODIMENTS

A detailed description of one preferred embodiment of an ophthalmic apparatus embodying the present invention will now be given referring to the accompanying drawings. In following description, an objective refractive power measurement apparatus of a handheld-type is adopted for the preferred embodiment.

Figure 1:
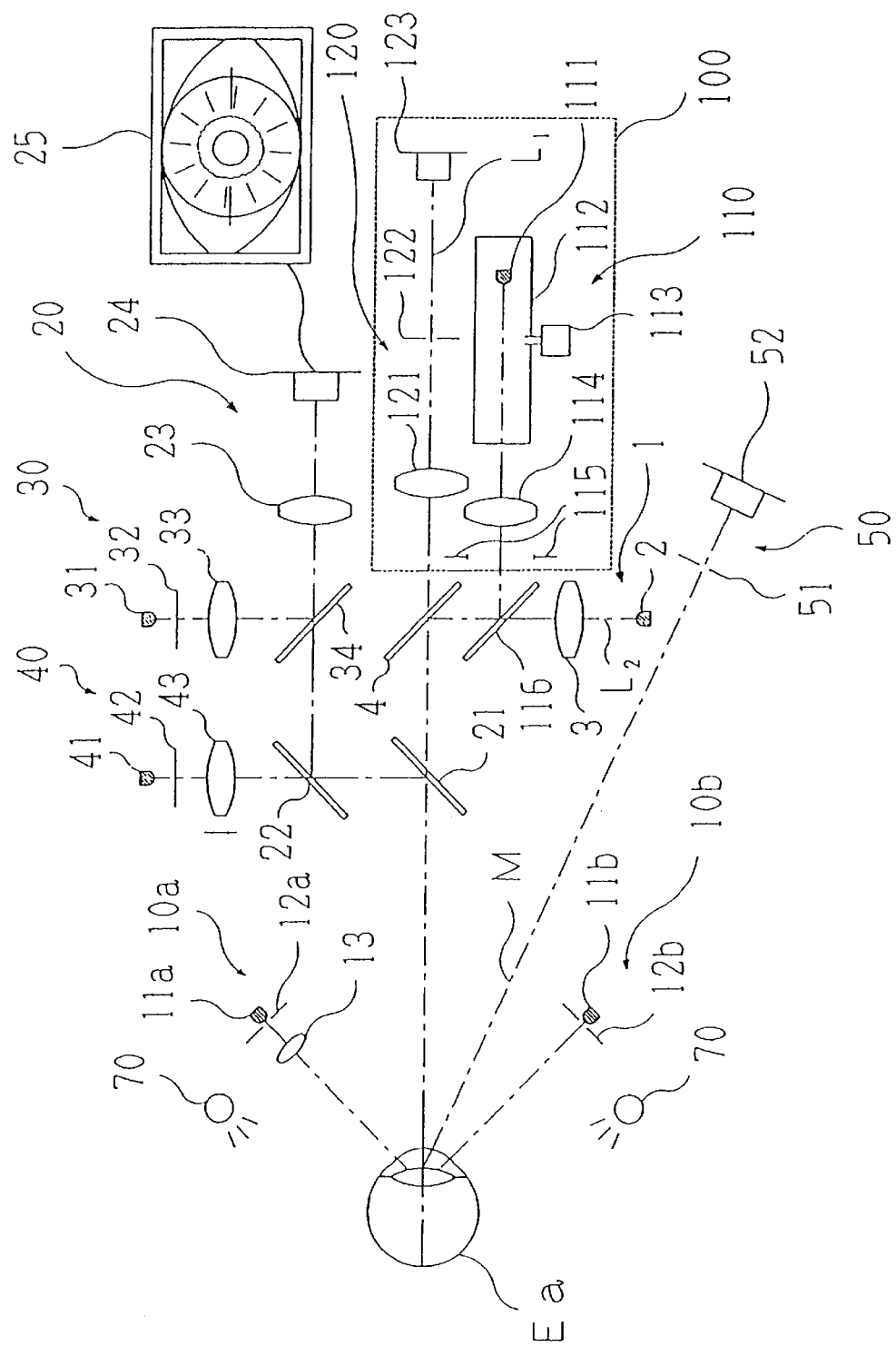
FIG. 1 is a side view showing a schematic arrangement of a part of an optical system of an apparatus according to the preferred embodiment of the present invention.

In FIG. 1, there is shown a side view of a schematic arrangement of a part of an optical system of an apparatus according to the preferred embodiment. The optical system consists of a front target-projecting optical system for a measuring eye, a distance-target projecting optical system, a target detecting and observing optical system, a reticle projecting optical system, a fixation-target projecting optical system, a refractive power measuring optical system, a front target-detecting optical system, a front target-projecting optical system for a non-measuring eye, and the like. Besides, in FIG. 1, the front target-projecting optical system for a non measuring eye is not shown in convenience.

Where, Ea is a measuring eye. L1 is an optical axis for measurement of a measuring optical system mentioned below. Numeral 70 is a light source by which an anterior part of the measuring eye Ea is illuminated.

(Front target-projecting optical system for a measuring eye)

Numeral 1 is a front target-projecting optical system for a measuring eye. Numeral 2 is a light source for aligning a measuring optical system roughly. Numeral 3 is a collimating lens which causes a luminous flux from the light source 2 to be approximately a parallel luminous flux. Numeral 4 is a beam splitter which causes an emitting axis L2 for a luminous flux of the light source 2 to coincide with the optical axis L1 for measurement. Luminous flux from the light source 2 is made to be approximately a parallel luminous flux by the collimating lens 3, then passes through a below-mentioned beam splitter 116, then is made to coincide with the optical axis L1 for measurement by the beam splitter 4, and then passes through a dichloic mirror 21, thereby being projected onto the measuring eye Ea.

(Distance-target projecting optical system)

Numerals 10a and 10b are distance-target projecting optical systems which project a target for detecting a working distance between the measuring eye Ea and the apparatus. The distance-target projecting optical system 10a consists of a light source 11a, a spot diaphragm 12a, and a collimating lens 13 which causes a luminous flux from a light source 11a to be approximately a parallel luminous flux. By such configuration, the system 10a projects the spot-diaphragm target onto the measuring eye Ea from an optical infinite distance. On the contrary, the distance-target projecting optical system 10b consists of a light source 11b and a spot diaphragm 12b. By such configuration, the system 10b projects the spot-diaphragm target onto the measuring eye Ea from an optical finite distance. The distance-target projecting optical systems 10a and 10b are disposed so that respective emitting axes thereof can intersect with the optical axis L1 for measurement with making the same angle (In FIG. 1, the measuring eye Ea is projected from an upper and a lower directions in convenience, however, it is preferable that the distance-target projecting optical systems 10a and 10b are disposed horizontally in order to prevent a luminous flux from being intercepted by an eyelash and an eyebrow).

(Target detecting and observing optical system)

Numeral 20 is a target detecting and observing optical system. An image of an anterior part of the eye by a light source 70, a corneal reflex by the front target-projecting optical system 1 for a measuring eye, and corneal reflexes by the distance-target projecting optical systems 10a and 10b are reflected by dichloic mirrors 21 and 22, then pass through a below-mentioned beam splitter 34, and then form an image on a photographing element of a camera 24 for observation by an image forming lens 23. In the preferred embodiment, a CCD camera for near infrared range is adopted for as the camera 24 for observation. An image of an anterior part of the eye and a corneal reflexes photographed by the camera 24 for observation are displayed on a TV monitor 25.

(Reticle projecting optical system)

Figure 2:
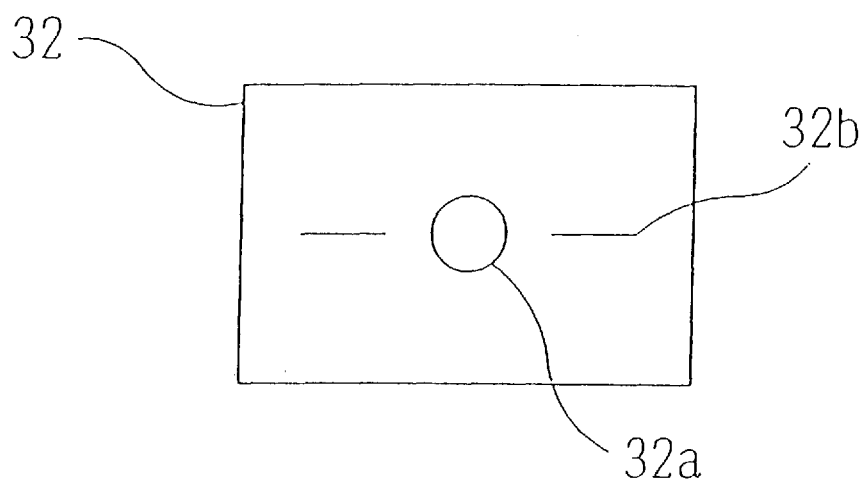
FIG. 2 is a view for illustrating a reticle mark provided for a reticle plate.

Numeral 30 is a reticle projecting optical system. Numeral 31 is a light source which illuminates a reticle plate 32. As shown in FIG. 2, a reticle mark is formed on the reticle plate 32. Numeral 32a is a circular reticle mark. Numeral 32b is a line mark of which an astigmatism axial angle of a measuring system indicates a direction of 0°. Alternatively, the line mark may not necessary for the apparatus. Or, alternatively, the line mark indicating a direction of 90° may be additionally provided thereon. Light passed through the reticle plate 32 passes through a projecting lens 33, then is reflected by the beam splitter 34, and then forms an image on the photographing element of the camera 24 for observation by the image forming lens 23. The image of the reticle mark photographed by the camera 24 for observation is displayed on the TV monitor 25.

(Fixation-target projecting optical system)

Numeral 40 is a fixation-target projecting optical system. Numeral 41 is a light source, 42 is a fixation target, and 43 is a projecting lens. The projecting lens 43 fogs the measuring eye Ea by moving in the direction of the optical axis. The fixation-target projecting optical system 40 is made to coincide with the target detecting and observing optical system 20 by the above-mentioned dichloic mirror 22. The light source 41 illuminates the fixation target 42 from which a luminous flux passes through the projecting lens 43 and the dichloic mirror 22, then is reflected by the dichloic mirror 21, and then reaches to the measuring eye Ea, thereby causing the measuring eye Ea to be fixed to the fixation target 42.

(Refractive power measuring optical system)

Numeral 100 is a refractive power measuring optical system. The refractive power measuring optical system 100 consists of a slit projecting optical system and a slit-image detecting optical system.

Figure 3:
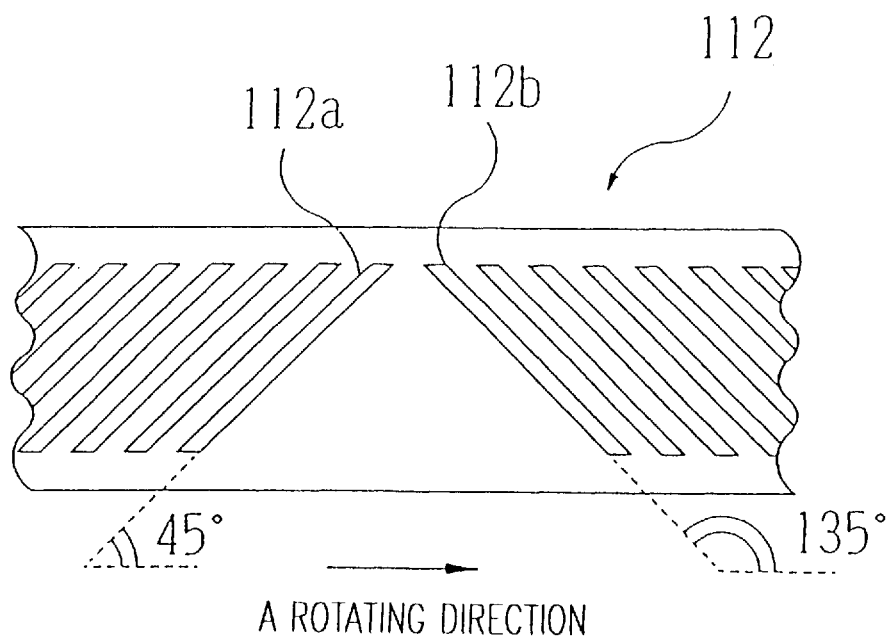
FIG. 3 is a view showing a developed view of a slit aperture provided for a side face of a rotation sector.

Numeral 110 is a slit projecting optical system. Numeral 111 is a slit illumination light source. Numeral 112 is a cylindrical rotation sector which rotates with a fixed velocity to a fixed direction by a motor 113. On the side face of the rotation sector 112, as shown in FIG. 3, a plurality of slit apertures 112a and 112b which have two kinds of different angle of inclination respectively are provided. The slit aperture 112a is disposed so as to have an angle 45° of inclination with a rotating direction of the rotation sector 112, and the slit aperture 112b is disposed so as to have an angle 135° of inclination with a rotating direction so as to intersect at right angles with the slit aperture 112a. Numeral 114 is a projecting lens, and the light source 111 is at conjugate position relative to a position close to a cornea of the measuring eye Ea with respect to the projecting lens 114. Numeral 115 is a limit diaphragm, and 116 is a beam splitter which causes the axis of the slit projecting optical system 110 to coincide with the axis of the front target-projecting optical system 1 for a measuring eye.

Light from the light source 111 illuminates the slit apertures 112a or the slit apertures 112b of the rotation sector 112. Slit luminous-flux scanned by rotation of the rotation sector 112 passes through the projecting lens 114, then is reflected by the beam splitter 116, thereby being made to coincide with the front target-projecting optical system 1 for a measuring eye, then is transmitted to the measuring eye Ea, then converges at the position close to the cornea of the measuring eye Ea, thus being projected onto a fundus of the measuring eye Ea. Besides, the rotation sector 112 has slit apertures having different angles, therefore, a sensor which is not shown is provided thereon in order to detect which slit luminous-flux is projected.

Figure 4:
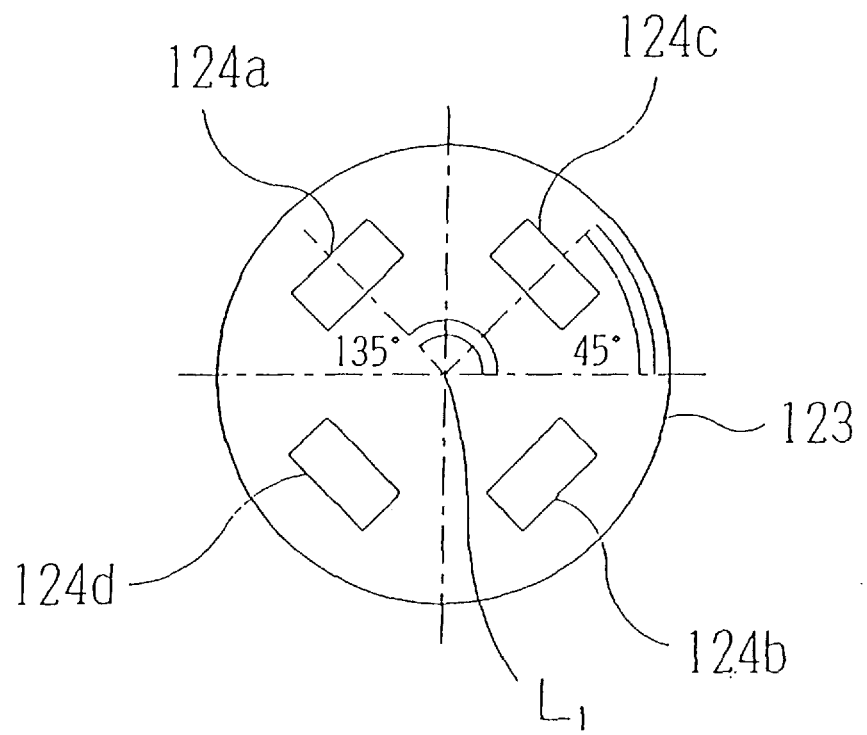
FIG. 4 is a view for illustrating an arrangement of four photo-detectors of photo-detecting part.

Numeral 120 is a slit image detecting optical system which includes a photo receiving lens 121, a diaphragm 122 and a photo-detecting part 123. The diaphragm 122 is disposed at the back focal point of the photo receiving lens 121, and the photo-detecting part 123 is disposed at conjugate position relative to the cornea of the measuring eye Ea with respect to the photo receiving lens 121. The photo-detecting part 123 is provided with four photo-detectors 124a–124d on the surface thereof as shown in FIG. 4. The photo-detectors 124a and 124b are disposed so as to be symmetric with the center at the optical axis L1 for measurement, in the same way, the photo-detectors 124c and 124d are disposed so as to be symmetric with the center at the optical axis L1 for measurement. These two pairs of photo-detectors are respectively made to be corresponding to a scanning direction of a slit luminous flux on the fundus of the measuring eye Ea which is projected by the slit apertures 112a and 112b having two kinds of angles of inclination (the slit luminous flux on the fundus comes to be scanned in a direction intersecting with a long direction of the slit at right angles, as it were). In the preferred embodiment, a pair of photo-detectors 124a and 124b are disposed so as to correspond to a direction intersecting at right angles with a long direction of the slit received by the photo-detecting part 123 at the time when the slit luminous flux from the slit apertures 112a is scanned on the fundus of the measuring eye Ea having hyperopia or myopia exclusive of astigmatism, in the same way, a pair of photo-detectors 124c and 124d are disposed so as to correspond to a direction intersecting at right angles with a long direction of the slit received by the photo-detecting part 123 at the time when the slit luminous flux from the slit apertures 112b is scanned thereon.

The slit projecting optical system 110 scans and projects respective slit-shaped luminous flux in two directions onto the fundus of the measuring eye Ea, and the slit image detecting optical system 120 detects the slit luminous flux reflected by the fundus with using a pair of photo-detectors 124a and 124b and a pair of photo-detectors 124c and 124d that are disposed at approximately a conjugate position relative to the cornea of the measuring eye Ea so as to be symmetric respectively with putting the optical axis therebetween. The photo-detectors 124a and 124b are disposed so as to correspond to a direction intersecting at right angles with a long direction of the slit in case a slit luminous flux in one direction is projected onto the measuring eye Ea having no astigmatism, and a corneal center or a center of a visual axis of the measuring eye Ea is detected based on an output signal of a phase difference from the photo-detectors 124c and 124d thereat. Based on the detected corneal center or the detected center of the visual axis, and respective output signals from the photo-detectors 124a and 124b disposed so as to be corresponding to above-mentioned one direction, a refractive power at each position corresponding to each photo-detector is calculated. Thereby a refractive power in a meridian direction relative to the corneal center or the center of the visual axis is calculated, and an existence of an irregular astigmatism is detected. In addition, a detailed description concerning a measurement for refractive power of an eye is disclosed by Japanese Patent Laid-Open No. Hei10-108836 corresponding to U.S. patent application Ser. No. 08/942,633 entitled "OPHTHALMIC MEASUREMENT APPARATUS".

(Front target-detecting optical system)

Figure 5:
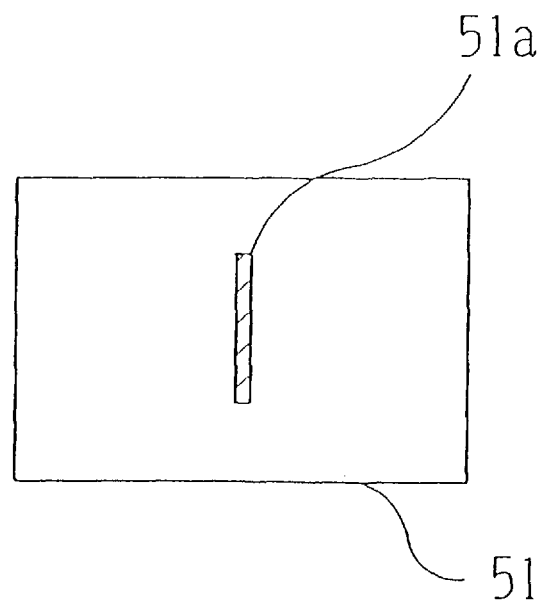
FIG. 5 is a view for illustrating a slit provided for a luminous flux diaphragm.

Numeral 50 is a front target-detecting optical system. Numeral 51 is a luminous flux diaphragm which limits a luminous flux M reflected by the cornea from the measuring eye Ea and a luminous flux N reflected by the cornea from the non-measuring eye Eb, and is provided with a slit 51a as shown in FIG. 5. The slit 51a is configured so that the luminous flux reflected by the cornea may be limited within a predetermined range also in a vertical direction. Numeral 52 is a two-dimensional positional detector which detects a slit luminous flux limited by the luminous flux diaphragm 51 (the slit 51a), for which a two-dimensional CCD camera for near infrared range is adopted in the preferred embodiment. The luminous flux diaphragm 51 is spaced apart by a predetermined distance from the positional detector 52 in a direction toward the eye, and the slit 51a is disposed so as to be approximately the center of the positional detector 52. In addition, the luminous flux diaphragm 51 and the positional detector 52 are disposed below the optical axis L1 for measurement (the emitting axis L2).

Figure 6:
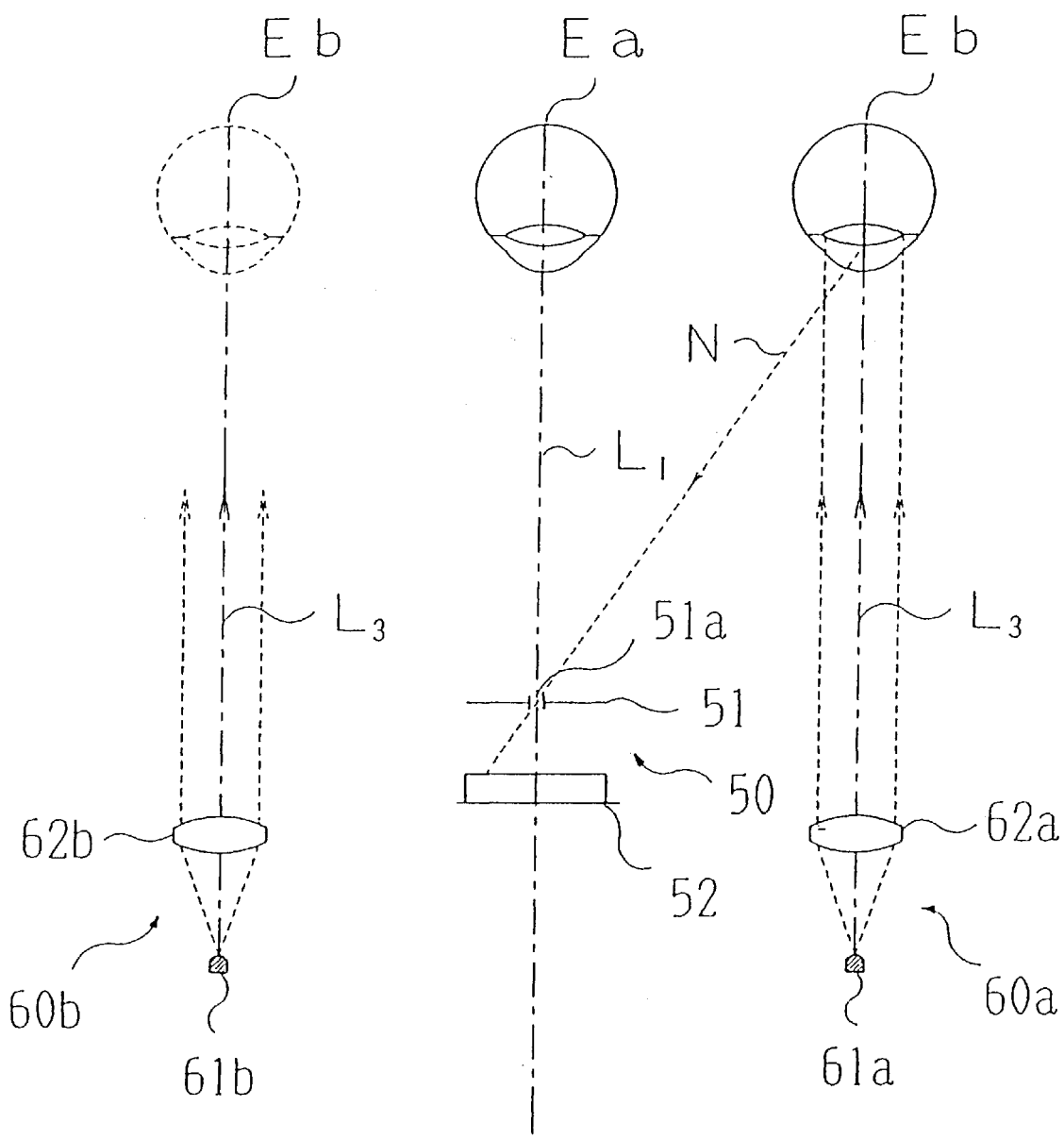
FIG. 6 is a top view showing a schematic arrangement of a part of an optical system of an apparatus according to the preferred embodiment of the present invention.

FIG. 6 is a top view showing a schematic arrangement of a part of an optical system of the apparatus according to the preferred embodiment. Besides, the front target-detecting optical system and the front target-projecting optical system for a non-measuring eye are only shown in convenience for illustrating, thus other optical systems are not shown.

(Front target-projecting optical system for a non-measuring eye)

Eb is a non-measuring eye, and numerals 60a and 60b are front target-projecting optical systems for a non-measuring eye. 60a is disposed at a right side of the apparatus from the examiner's sight, and 60b is disposed at a left side from the examiner's sight. Numerals 61a and 61b are light sources which emit a luminous flux onto the non-measuring eye Eb. Numerals 62a and 62b are collimating lens which cause the luminous flux from the light sources 61a and 61b to be approximately a parallel luminous flux. L3 is an emitting axis of the front target-projecting optical systems 60a and 60b for a non-measuring eye. In order to magnify a measuring range, it is necessary to enlarge a diameter of a luminous flux for measurement relatively, in this case, it is desirable that a distance between the optical axis L1 (the emitting axis L2) and the emitting axis L3 is approximately 64 mm corresponding to an averaged interpupillary distance. N is a luminous flux reflected by the cornea from the non-measuring eye Eb.

In addition, LEDs which emit luminous flux within a range of near infrared ray are adopted as the light sources 2, 11, 31, 61a, 61b, 70 and 111, accordingly, a luminous flux can be emitted without troubling the eyes Ea and Eb with a burden.

Next, the operation of the apparatus will be described below with reference to FIG. 7. In the following, a description is made by dividing into an operation for judging whether the measuring eye is a right eye or a left eye and an operation for measuring an interpupillary distance of the examinee.

(Operation for judging whether a measuring eye is a right eye or a left eye)

Firstly, the apparatus is made to be moved in front of the measuring eye Ea, then the light source 70 for illuminating an anterior part of the eye, and the light sources 2 and 31 for alignment are made to be emitted by using switches not shown, or the like. An image of an anterior part of the eye by the light source 70, a corneal reflex formed on the measuring eye Ea by the light source 2 and an image of a reticle mark by a reticle projecting optical system 30 are photographed by the camera 24 for observation, then is displayed on the TV monitor 25. Further, the examiner causes the apparatus to move so that the corneal reflex by the light source 2 can be positioned at the center of the reticle mark 32a with observing the image of the corneal reflex and the image of the reticle mark displayed on the TV monitor 25, thus causing an alignment to be performed in vertical and lateral directions. In addition, when the line mark 32b is provided, the examiner adjusts an inclination of the apparatus with observing the TV monitor 25 so that the image of the line mark 32b may be horizontal.

When it is confirmed that the corneal reflex detected by using an image processing technique is in a predetermined area and that the alignment of the measuring eye Ea in lateral and vertical directions is completed, then a control part causes the light source 61a or 61b to emit a light, thereby emitting a luminous flux within a range of near infrared ray onto the non-measuring eye Eb. Simultaneously, the control part causes the light source 70 to be turned off. Luminous flux emitted onto the non-measuring eye Eb is transmitted into the non-measuring eye Eb, thereby causing a corneal reflex to be formed. The luminous flux reflected by the cornea from the non-measuring eye Eb passes through the slit 51a of the luminous flux diaphragm 51, then is transmitted into the positional detector 52.

If the positional detector 52 does not detect the luminous flux reflected by the cornea in response to emission of the light source 61a (or 61b), then the control part causes the opposite light source 61b (or 61a) to emit a light. If the positional detector 52 detects the luminous flux reflected by the cornea in response to emission of the light source 61a, then the eye is proved out to be a right eye. If the positional detector 52 detects the luminous flux reflected by the cornea in response to emission of the light source 61b, then the eye is proved out to be a left eye.

Alternatively, instead of making the light sources 61a and 61b emit separately, the light sources 61a and 61b may be made to emit a light simultaneously. In this case, it is capable of judging whether the measuring eye is a right eye or a left eye based on the side either right or left at which the luminous flux reflected by the cornea is detected relative to the center of the positional detector 52. If the luminous flux reflected by the cornea is detected at a left side relative to the center of the positional detector 52 in the examiner's sight, then it is proved out that the eye is a right eye, and if it is detected at a right side in the examiner's sight, then it is proved out that the eye is a left eye.

Although the alignment in lateral and vertical directions is completed, if the positional detector 52 does not detect the luminous flux reflected by the cornea in response to emission both of the light sources 61a and 61b, then there is high possibility that the apparatus or the eye to be examined is inclined, then, the examiner is warned by a warning sound or an error massage on the TV monitor 25. The examiner adjusts inclination of the apparatus and causes the light source 61a or 61b (or 61a and 61b simultaneously) to emit a light by using a switch not shown, or the like. In this case, if the line mark 32b is provided, then the examiner adjusts inclination of the apparatus once again so that the eye may be horizontal relative to the line mark 32b with observing the TV monitor 25. In addition, in case that inclination detected by using a level is in excess of a predetermined standard, a warning may be given to the examiner by a warning sound or a display on the TV monitor 25. Further, only in case that inclination detected by using a levels is within a predetermined standard, the light source 61a or 61b may be made to emit a light(or simultaneously).

(Measurement of an interpupillary distance)

Firstly, the apparatus is moved in front of the measuring eye Ea, then the light source 70 for illuminating the anterior part of the eye, and the light sources 2 and 31 for an alignment are made to emit a light. An image of an anterior part by the light source 70, the corneal reflex formed on the measuring eye Ea by the light source 2 and the image of the reticle mark by the reticle projecting optical system 30 are photographed by the CCD camera 24 for observation, then are displayed on the TV monitor 25. The examiner makes the apparatus move further so that the corneal reflex by the light source 2 can be positioned at the center of the reticle mark 32a with observing the corneal reflex and the image of the reticle mark on the TV monitor 25, thereby the alignment is performed in lateral and vertical directions. In addition, in case that the line mark 32b is provided, the examiner adjusts an inclination of the apparatus with observing the TV monitor 25 so that the image of the line mark 32b may be horizontal.

Figure 8A:
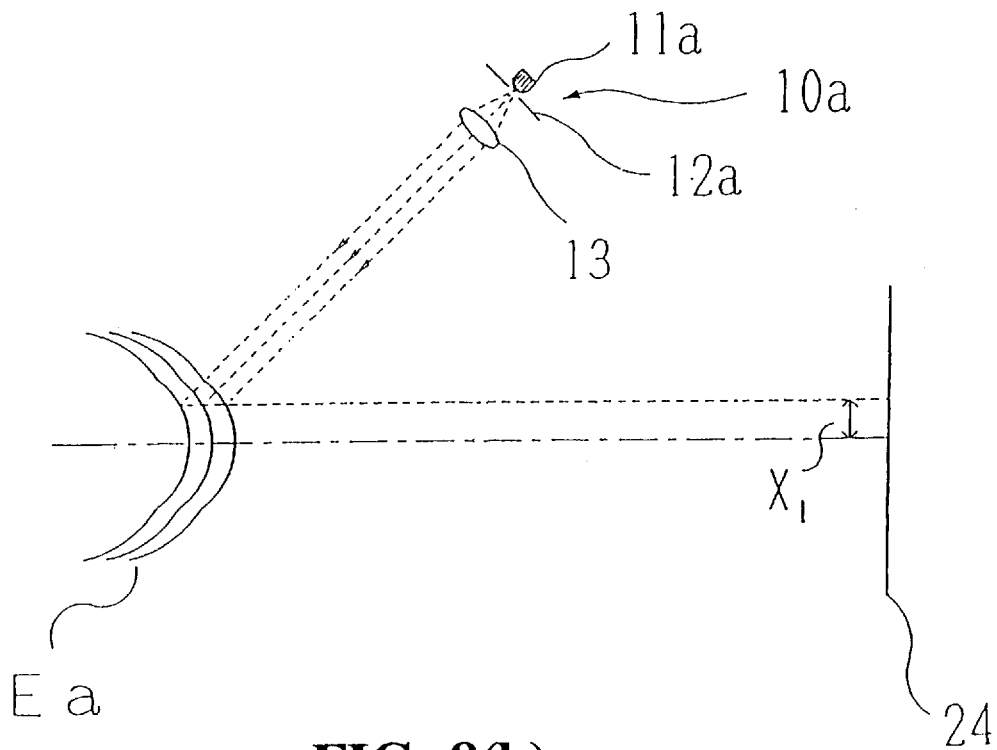
FIGS. 8(a) and 8(b) are views for illustrating a method for aligning an eye to be examined in a direction of a working distance.
Figure 8B:
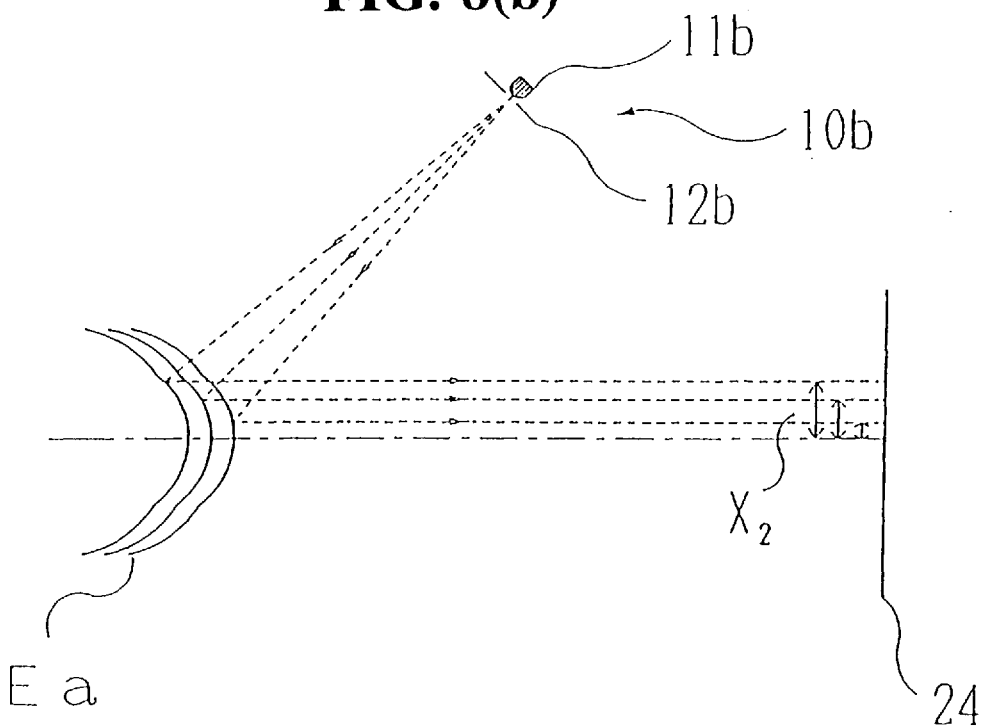

Further, the examiner brings the corneal reflex of the measuring eye Ea into focus, then roughly judges a working distance. While roughly adjusting a working distance, the apparatus judges suitability of the working distance by using the distance-target projecting optical systems 10a and 10b. In this case, the apparatus compares the height of the corneal reflexes formed by the distance-target projecting optical systems 10a and 10b. As shown in FIGS. 8(a) and 8(b), a luminous flux from the distance-target projecting optical system 10a is made to be approximately a parallel luminous flux by the collimating lens 13, therefore, the light source 11a comes to be at an infinite distance optically, accordingly, even if the working distance changes, then the height X1 of the corneal reflex does not changes (see FIG. 8(a)). On the contrary, a luminous flux from the distance-target projecting optical system 10b is not made to be approximately a parallel luminous flux, therefore, the light source 11b comes to be at a finite distance optically, accordingly, if the working distance changes, then the height X2 of the corneal reflex changes (see FIG. 8(b)). The working distance is set so as to satisfy the expression X2/X1=$\alpha$, where $\alpha$ is a constant. Then, the values X1 and X1 are detected to calculate, thereby a focal shift can be detected as following.

(1) X2/X1>$\alpha$: Cornea shifts to a front side.
(2) X2/X1<$\alpha$: Cornea shifts to a back side.
(3) X2/X1=$\alpha$: Completion of alignment (positional adjustment).

Alternatively, the value $\alpha$ may be in an allowable range to some extent considering the required accuracy for the alignment. In case that a calculated result satisfies above identified expression (1) or (2), its shifting condition is displayed on the TV monitor 25. The examiner moves the apparatus in accordance with the display until it is displayed on the TV monitor 25 that the condition is changed to above identified expression (3).

If it is confirmed that the height of the corneal reflexes detected by the image processing technique satisfies the predetermined relationships and that the alignment with the measuring eye Ea in the working distance direction is performed, then the control part causes the light source 61a (or 61b) at the eye Eb's side to emit a light(or causes the light sources 61a and 61b to emit a light simultaneously). Simultaneously, the control part causes the light sources 11 and 70 to be turned off. Luminous flux from the light source 61a (or 61b) is made to be approximately a parallel luminous flux by the collimating lens 62a (or 62b), then is transmitted into the non-measuring eye Eb.

A part of the luminous flux reflected by the cornea from the measuring eye Ea caused by the alignment light from the light source 2 is made to be a slit luminous flux which is limited by the slit 51a which is provided for the luminous flux diaphragm 51, and is transmitted into the positional detector 52, thereby forming a slit image. The slit 51a is disposed at the center relative to the positional detector 52, therefore, the slit image by the luminous flux reflected by the cornea of the measuring eye Ea is formed at the center of the positional detector 52.

On the contrary, the luminous flux reflected by the cornea from the non-measuring eye Eb caused by the light source 61a (or 61b) is also made to be a slit light which is limited by the slit 51a which is provided for the luminous flux diaphragm 51, then is transmitted into the positional detector 52, thereby forming the slit image. In case of FIG. 6, the non-measuring eye Eb forms a luminous flux reflected by the cornea by using a luminous flux from the light source 61a, therefore, the luminous flux reflected by the cornea from the non-measuring eye Eb is transmitted into a left side relative to the center of the positional detector 52 in the examiner's sight.

Although the alignment with the measuring eye Ea is completed, the positional detector 52 does not detect a luminous flux reflected by the cornea in response to emission both of the light sources 61a and 61b, there is high possibility that the apparatus or the eye to be examined is inclined, then, the examiner is warned by a warning sound or an error massage on the TV monitor 25. The examiner adjusts inclination of the apparatus in the same manner as above described.

On the positional detector 52, two slit images are formed by the luminous flux reflected by the cornea from the eyes Ea and Eb. Accordingly, by measuring a distance between two slit images, a distance between the measuring eye Ea and Eb can be proved out.

Figure 9:
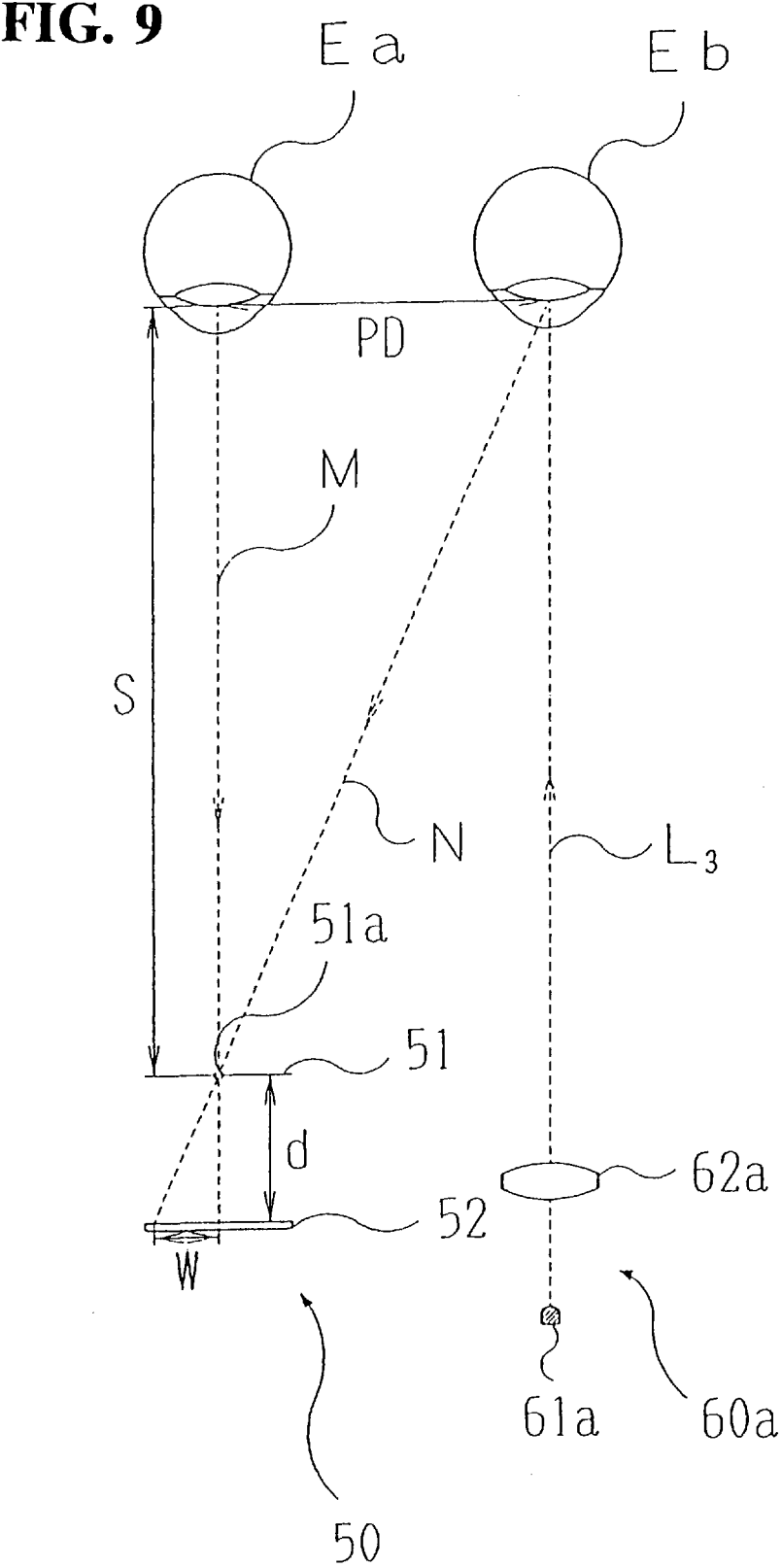
FIG. 9 is a view for illustrating a method for measuring an interpupillary distance of an examinee.

The method for measuring an interpupillary distance will be described below in detail with reference to FIG. 9.

An interpupillary distance of the examinee between the corneal reflex of the measuring eye Ea and that of the non-measuring Eb is defined as PD, a distance between the corneal reflex of the measuring eye Ea and the luminous flux diaphragm 51 (the slit 51a) is defined as S, a distance between the luminous flux diaphragm 51 (the slit 51a) and the positional detector 52 (a slit image caused by a luminous flux reflected by the cornea from the measuring eye Ea) is defined as d, and a distance in a lateral direction between a slit image caused by a luminous flux reflected by the cornea from the measuring eye Ea on the positional detector 52 and a slit image caused by a luminous flux reflected by the cornea from the eye Eb thereon is defined as W.

Where, a value d is a known value which is set by design, a value S is a set value of a working distance of the apparatus at the time when being aligned with the measuring eye Ea exactly. And, referring to FIG. 9, the following expression is given.

$PD:W=S:d$

Therefore, the following expression is given based on the above relationship.

$PD*d=W*S$

Further, the following expression is given.

$PD=W*S/d$

Therefore, the slit image caused by the luminous flux reflected by the cornea from the measuring eye Ea on the positional detector 52 and the slit image caused by the luminous flux reflected by the cornea from the eye Eb thereon are detected, and the value W which is a distance in a lateral direction between two slit images is calculated, then the obtained values are substituted for above identified expression, thereby the value PD (an interpupillary distance of the examinee) can be found.

A position of the corneal reflex in a lateral direction, which is formed by emitting approximately a parallel luminous flux onto the eye Eb, changes in accordance with a corneal curvature (which differs with individual difference) and a position of the eye Eb (which differs with individual difference of PD) opposite to the light source 61a (or 61b), however, an amount of change is unconsidered value being compared with accuracy required for measuring an interpupillary distance. This is the reason why to propose the above-mentioned detecting method and calculating method.

In generally, the refractive power measurement is performed plural times. For example, every time when the refractive power measurement is performed, then the measurement of an interpupillary distance is performed, further, the eye is changed to the other eye, then it is measured. These data are averaged, thereby the accuracy is made to be higher, and is outputted (displaying, printing out, and the like).

In the above described embodiment, a judgement whether the eye is right or left and a measurement of an interpupillary distance are performed by detecting the slit image, however, respective operations may be performed independently or simultaneously. In case of performing simultaneously, after the alignment in directions of lateral, vertical and a working distance is completed, then a judgement whether the eye is right or left and a measurement of an interpupillary distance may be performed simultaneously. In other words, the light source 61a or 61b is made to emit a light (or 61a and 61b simultaneously) in order to judge whether the eye is right or left, thereby if the slit image by the luminous flux reflected by the cornea from the non-measuring eye Eb is detected by the positional detector 52, then a measurement of an interpupillary distance can be performed by using the slit image.

In above description, a two-dimensional positional detector is utilized for the positional detector 52, however, the one-dimensional positional detector (CCD, PSD or the like) is enough to judge whether the eye is right or left and to measure an interpupillary distance. The two-dimensional positional detector is particularly suitable for below identified practical use.

That is, if a position of the slit image by the luminous flux reflected by the cornea from the measuring eye Ea, a position of the slit image by the luminous flux reflected by the cornea from the non-measuring eye Eb are detected by the two-dimensional positional detector, then a detection of the inclination of the apparatus and a correction of an astigmatism axial angle for use in measuring a refractive power, a corneal curvature and the like can be performed in addition to a judgement whether the eye is right or left and a measurement of an interpupillary distance. Details will be described below with reference to FIGS. 10(a) and 10(b).

Figure 10A:
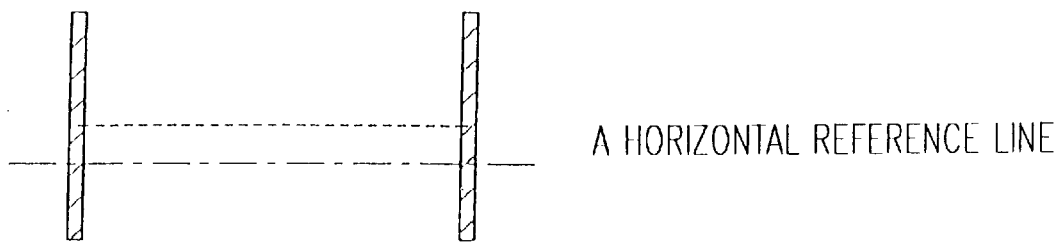
FIGS. 10(a) and 10(b) are views for illustrating a method for detecting an axial angle of an eye to be examined.
Figure 10B:
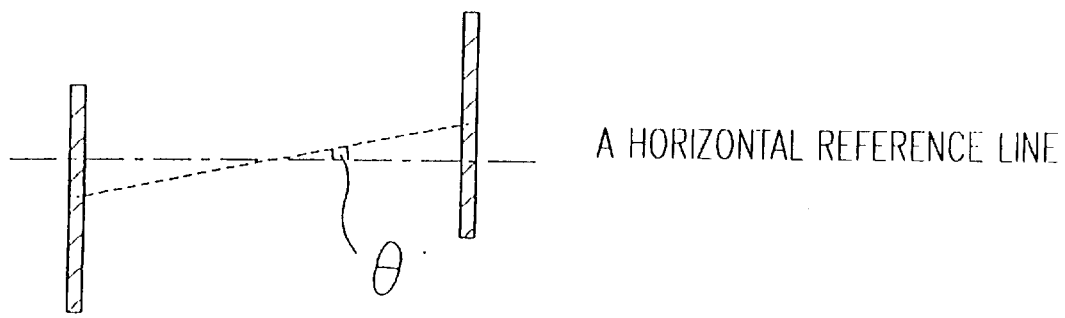

FIG. 10(a) shows that a line connecting two slit images caused by two luminous flux reflected by the cornea from the eyes Ea and Eb (in the preferred embodiment, a line connecting respective center points of two slit images) is parallel relative to a horizontal reference line of the apparatus (a long direction of the photographing element is corresponding to a horizontal direction). On the contrary, FIG. 10(b) shows that a line connecting two slit images caused by two luminous flux reflected by the cornea from the eyes Ea and Eb is at an angle of an inclination θ relative to a horizontal reference line of the apparatus. In this case, the inclination θ made by a line connecting two slit images and a horizontal reference line of the apparatus is detected and calculated. An angle of the obtained inclination θ is displayed on the TV monitor 25 as a numeric or a pattern. Therefore, the examiner can easily know the inclination of the apparatus, and can correct the inclination of the apparatus. In addition, if a measurement result is utilized for calculating correction of an axial angle, then a correct axial angle can be obtained even though there is an inclination to some extent.

Besides, a well known method can be applied for the alignment with the eye in directions of lateral, vertical and a working distance, other than the method adopted for the preferred embodiment.

Figure 11:
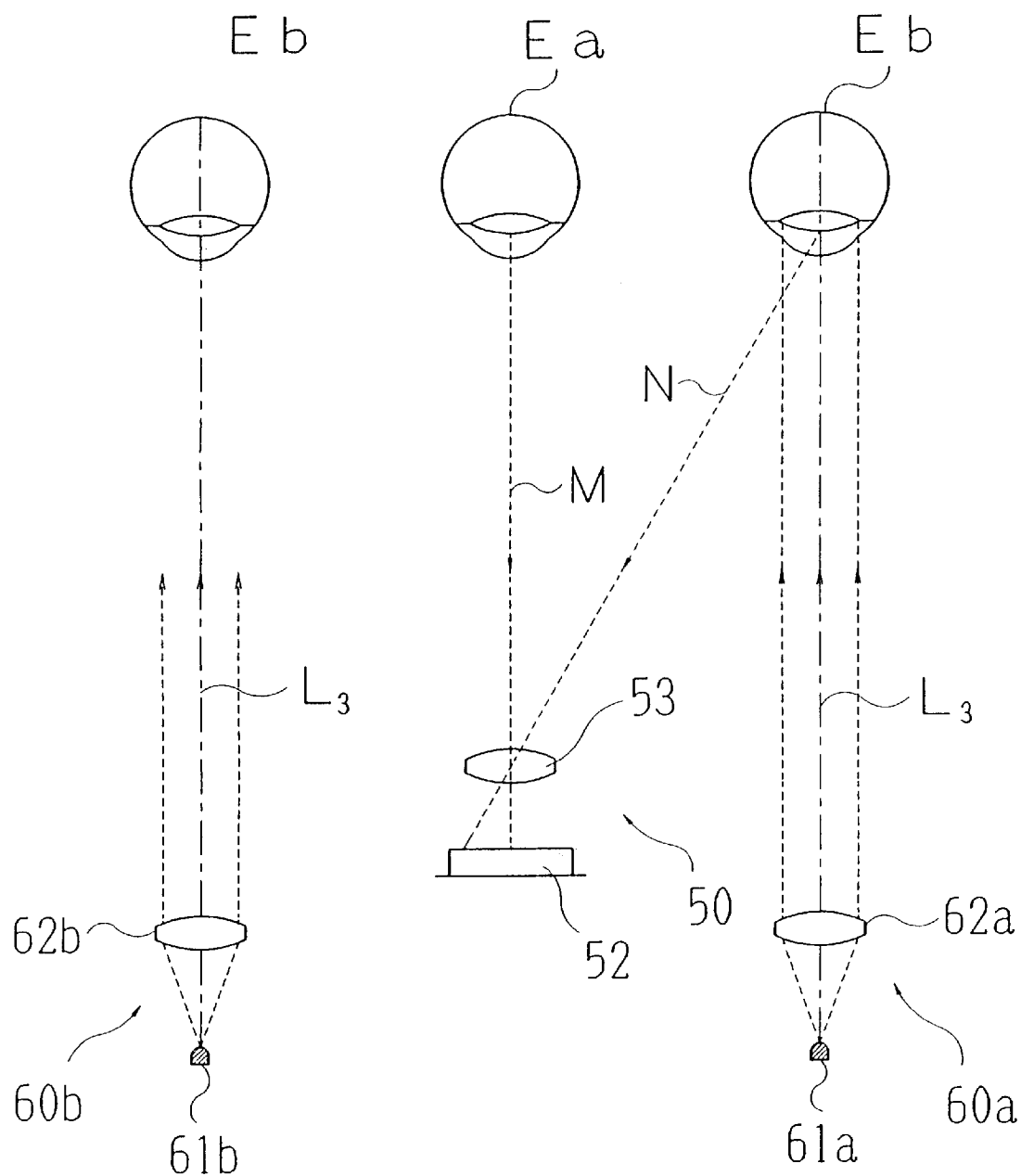
FIG. 11 is a top view showing a schematic arrangement of a part of an optical system of an apparatus according to the modification of the preferred embodiment of the present invention.

In addition, in the preferred embodiment, the luminous flux diaphragm 51 is provided for limiting the luminous flux M reflected by the cornea from the measuring eye Ea and the luminous flux N reflected by the cornea from the non-measuring eye Eb, alternatively, the focusing lens 53 may be utilized instead of the luminous flux diaphragm 51 (see FIG. 11). In this case, the corneal reflex and the positional detector 52 are conjugate with respect to the focusing lens 53. If the focusing lens 53 is utilized instead of the luminous flux diaphragm 51, then an amount of the luminous flux reflected by the cornea to be detected may be stable.

In addition, in the preferred embodiment, a right eye and a left eye are classified into the measuring eye and the non-measuring eye respectively, however, the present invention is not restricted to the apparatus which measures only one eye. The present invention is utilized for the apparatus having a measurement system for both eyes.

Further, the present invention is not restricted to the hand-held type ophthalmic apparatus, it is also utilized for the setting-type ophthalmic apparatus.

The foregoing description of the preferred embodiments of the invention has been presented for purposes of illustration and description. It is not intended to be exhaustive or to limit the invention to the precise form disclosed, and modifications and variations are possible in the light of the above teachings or may be acquired from practice of the invention. The embodiments chosen and described in order to explain the principles of the invention and its practical application to enable one skilled in the art to utilize the invention in various embodiments and with various modifications as are suited to the particular use contemplated. It is intended that the scope of the invention be defined by the claims appended hereto, and their equivalents.

What is claimed is:

1. An ophthalmic apparatus having an examining unit which examines an eye to be examined, the apparatus comprising:

alignment means for aligning said examining unit with each of a right eye and a left eye, including a target optical system which forms an alignment target on one eye;

corneal reflex forming means including an emitting optical system by which a corneal reflex is formed on the other eye, in which said emitting optical system emitting a luminous flux on relatively wide area where is defined based on dispersion of an interpupillary distance of an examinee, and an optical axis of said emitting optical system and an optical axis of said examining unit being spaced at a predetermined distance;

a detecting optical system for detecting a corneal reflection being in a direction intersecting with the optical axis of said emitting optical system, including limiting means which limits incidence of the corneal reflection and positional detecting means which detects a position of the limited corneal reflection; and calculating means for judging whether the aligned eye is a right eye or a left eye and/or calculating an interpupillary distance thereof, based on results detected by said detecting optical system.

2. The ophthalmic apparatus according to claim 1, wherein said limiting means is each of a diaphragm and a lens.

3. The ophthalmic apparatus according to claim 1, wherein said emitting optical system includes a light source and an optical element which causes a luminous flux thereof to be approximately a parallel luminous flux.

4. The ophthalmic apparatus according to claim 1, wherein said detecting optical system also detects a position of a luminous flux of said alignment target, and said calculating means judges whether the eye is a right eye or a left eye and/or calculates an interpupillary distance thereof, based on a position of the luminous flux of said alignment target and a position of the corneal reflection of said emitting optical system.

5. The ophthalmic apparatus according to claim 1, wherein a pair of said corneal reflex forming means is provided for each side of said examining unit respectively.

6. The ophthalmic apparatus according to claim 1, wherein said positional detecting means is a two-dimensional photo detector which detects a position of the corneal reflection in lateral and vertical directions, which is limited by said limiting means; and the apparatus further comprising:

calculating means for calculating a relative angle of inclination between the apparatus and the eye based on the position in lateral and vertical directions which is detected by said positional detecting means.

7. The ophthalmic apparatus according to claim 6, further comprising:

correcting means for correcting results measured by a measuring optical system and/or informing means for informing of a relative inclination between the apparatus and the eye, based on the relative angle of inclination between the apparatus and the eye calculated by said calculating means.

8. The ophthalmic apparatus according to claim 1, the apparatus comprises a case of a hand-held type.

9. An ophthalmic apparatus having an alignment target projecting optical system for projecting an alignment target onto a measuring eye in order to align a measuring optical system with the measuring eye, a distance-target projecting optical system for projecting a distance target onto the measuring eye in order to detect a working distance relative to the measuring eye, and a target detecting optical system for detecting respective corneal reflex formed by said both projecting optical systems, the apparatus comprising:

a front target-detecting optical system for a measuring eye for detecting a part of a luminous flux reflected by the cornea from the measuring eye, which is caused by said alignment target projecting optical system;

an emitting optical system for a non-measuring eye for emitting a luminous flux on a non-measuring eye;

a front target-detecting optical system for a non-measuring eye for detecting a luminous flux reflected by the cornea from the non-measuring eye, which is caused by said emitting optical system for a non-measuring eye;

judging means for judging whether the measuring eye is a right eye or a left eye, based on a detected signal from said front target-detecting optical system for a non-measuring eye; and calculating means for calculating an interpupillary distance between the measuring eye and the non-measuring eye, based on detected signals from said both front target-detecting optical systems and said detected working distance.

10. The ophthalmic apparatus according to claim 9, wherein a target detecting means of said front target-detecting optical system for a measuring eye is also served as a target detecting means of said front target-detecting optical system for a non-measuring eye.

11. The ophthalmic apparatus according to claim 9, wherein said emitting optical system for a non-measuring eye is provided for each side of said alignment target projecting optical system.

12. The ophthalmic apparatus according to claim 9, further comprising:

warning means for warning the examiner when said judging means is disabled from judging whether the measuring eye is a right eye or a left eye based on the detected signal from said front target-detecting optical system for a non-measuring eye.

13. The ophthalmic apparatus according to claim 9, further comprising:

detecting means for detecting a relative inclination between the apparatus and the measuring eye; and warning means for warning the examiner that the apparatus inclines when it is judged by said detecting means that the relative inclination between the apparatus and the measuring eye is not appropriate.

14. The ophthalmic apparatus according to claim 9, further comprising:

detecting means for detecting a relative inclination between the apparatus and the measuring eye; and control means for causing a light source of said emitting optical system for a non-measuring eye to emit a luminous flux when it is judged by said detecting means that the relative inclination between the apparatus and the measuring eye is appropriate.

15. The ophthalmic apparatus according to claim 9, further comprising:

alignment judging means for judging suitability of the alignment in lateral and vertical directions based on an image of the alignment target detected by said target detecting optical system.

16. The ophthalmic apparatus according to claim 15, further comprising:

control means for causing a light source of said emitting optical system for a non-measuring eye to emit a luminous flux when it is judged by said alignment judging means that the alignment in vertical and lateral directions is appropriate.

17. The ophthalmic apparatus according to claim 9, further comprising:

working distance judging means for judging suitability of a working distance based on an image of the distance target detected by said target detecting optical system.

18. The ophthalmic apparatus according to claim 17, further comprising:

control means for causing a light source of said emitting optical system for a non-measuring eye to emit a luminous flux when it is judged by said working distance judging means that the working distance is appropriate.

19. The ophthalmic apparatus according to claim 9, wherein said measuring optical system is a refractive power measuring optical system.

20. The ophthalmic apparatus according to claim 9, the apparatus comprises a case of a hand-held type.

* * * * *